United States Patent [19]
Miller et al.

[11] Patent Number: 6,022,345
[45] Date of Patent: *Feb. 8, 2000

[54] METHOD AND APPARATUS FOR LASER-ASSISTED HAIR TRANSPLANTATION

[76] Inventors: Iain D. Miller, 36 Mystic St., Apt. 2, Charlestown, Mass. 02129; Karolj Nemes, Bratov Ucakar 84, 1000 Ljubljana, Slovenia

[*] Notice: This patent is subject to a terminal disclaimer.

[21] Appl. No.: 09/132,380

[22] Filed: Aug. 11, 1998

Related U.S. Application Data

[62] Division of application No. 08/820,761, Mar. 19, 1997
[60] Provisional application No. 60/014,418, Mar. 29, 1996.

[51] Int. Cl.[7] .................................................... A61B 17/36
[52] U.S. Cl. ................................... 606/9; 606/16; 606/19
[58] Field of Search .................................. 606/2, 3, 9, 10, 606/11, 12, 14, 15, 16, 17

[56] References Cited

PUBLICATIONS

Burkes et al., "Wet versus dry enamel ablation by Er."YAG laser, *The J. of Prosthetic Dentistry (Research and Education)*, 67(6):847–851 (1992).

J.T. Walsh, Jr. and J.P. Cummings, "Effect of the Dynamic Optical Properties of Water on Midinfraraed Laser Ablation," *Lasers in Surgery and Medicine*, 15:295–305 (1994).

W.P. Unger and L.M. David, "Laser Hair Transplantation," *J. of Dermatologic Surgery and Oncology*, 20(8):515–521 (1994).

J.M. Grevelink and J.B. Brennick, "Hair Transplantation Facilitated By Flashscanner–Enhanced Carbon Dioxide Laser," *Obj. Tech. Oto. Head Neck Surg*, 5(4) (1994).

Lukac et al., "Optoacoustic Effects during Er: YAG Laser Ablation in Hard Dental Tissue," *SPIE, Proceedings of Medical Applications of Lasers II*, 2327:93–100 (1994).

Kaufmann et al., "Cutting and Skin–Ablative Properties of Pulsed Mid–Infrared Laser Surgery," *J. Dermatol. Surg. Oncol.*, 20:112–118 (1994).

Raimund Hibst and Ulrich Keller, "Effects of water sapry and repetition rate on the temperature elevation during ER:YAG laser ablation of dentine," *SPIE*, 2623:139–144 (1987).

*Primary Examiner*—Linda C. M. Dvorak
*Assistant Examiner*—Sonya Harris-Ogugua
*Attorney, Agent, or Firm*—Lahive & Cockfield, LLP

[57] ABSTRACT

A laser treatment method and apparatus is provided which facilitates the grafting of hairs on the skin of a living human. The methodology involves a carefully designed treatment protocol utilizing a modified optical apparatus. The apparatus is a modified erbium-based laser system, designed for optimal therapeutic selectivity.

23 Claims, 3 Drawing Sheets

METHOD AND APPARATUS FOR LASER-ASSISTED HAIR TRANSPLANTATION

CLAIM TO BENEFIT OF EARLIER FILING DATE

This application is a divisional application of Ser. No. 08/820,761 filed on Mar. 19, 1997. The contents of the aforementioned application are hereby incorporated by reference.

This application claims the benefit of the prior filed co-pending provisional application Ser. No. 60/014418, filed on Mar. 29, 1996 for "Use of the Er:YAG laser for hair transplantation".

FIELD OF THE INVENTION

The present invention is directed to the practice of skin ablation and in particular to the transplantation of micrografts and minigrafts of hair on the skin utilizing a modified high power erbium laser system under carefully controlled conditions.

BACKGROUND

Over 1000 practitioners undertake hair transplantation in the United States, principally utilizing conventional techniques.

Under a conventional approach a scalpel or trephine punch is used to graft and implant circular or rectangular hair bearing areas. Typically, hair bearing areas from the rear of the scalp containing one or several hair follicles are removed and transplanted to the alopecic (bald) site.

These hair bearing tissue samples are then manually positioned in recipient sites consisting of previously prepared craters or incisions in the tissue. Such historical surgical approaches have utilized round and slit shaped recipient site preparation. Round recipient sites are prepared with circular punches, while slit-shaped recipient sites are prepared with surgical scalpels. Round grafts have been favored for higher graft density, while slit grafts present a more natural profile. Hair may be transplanted as micrografts containing 1–2 hairs or as minigrafts containing 4–5 hairs. The typical recipient site will be prepared to a tissue depth of approximately 3 mm.

Several disadvantages attend conventional hair transplantation techniques. Round grafts can appear 'clumpy' and unnatural, while slit grafts can compress the transplanted hair, creating a raised, unnatural appearance, especially with darker, coarser hair. This is a consequence of the fact that the scalpel is not removing a section of alopecic scalp, but rather creating a gaping slit, of typical length 5–6 mm. Further, the compression may be associated with hypoxia and hair growth failure.

It has been suggested (Unger, W. P., Journ. Derm. Surg. Oncol., 20, 8, 1994) that the precise removal of a section of alopecic scalp tissue would eliminate any compression, while simultaneously presenting the potential for a higher density of transplanted hair, since alopecic scalp would actually be removed. These factors, together with the potential reduction of operative bleeding, led to the initiation of trials in 1992 of laser induced slit transplant preparation using mid infra-red $CO_2$ lasers emitting at 10.6 µm. Such laser assisted hair transplantation has been reported using carbon dioxide lasers in superpulsed or scanned mode. Under such techniques, hair bearing sites are removed and prepared as before, while the laser is used to prepare the recipient site.

In the first reported study (Unger, W. P., Journ. Derm. Surg. Oncol., 20, 8, 1994), Unger described treatment of a limited number of patients using a superpulsed $CO_2$ laser, with up to 450 mJ applied at 12–15 Watt average power along a line 0.2 mm wide by 3 mm long. Here, the laser was traced along a series of such interweaving lines, which immediately gape to 0.5 mm, with superficial de-epithelialization and proximal tissue damage. Crater depth was not reported.

While the pulsed $CO_2$ laser was capable of hemostatic injury, Unger found it useful to increase the applied fluence to create some minimal bleeding, to better retain the transplanted hairs. Bleeding is indicative of the good vascular supply necessary to ensure graft take. In the absence of such, Unger noticed a significant failure rate. Results were acceptable at high fluence levels, although regrowth of hair was delayed by some 2–6 weeks when compared with scalpel slits, probably due to proximal tissue necrosis.

Continuous wave $CO_2$ lasers have also been used for hair transplantation. Grevelink has described (Grevelink, J. M., Obj. Tech. Oto. Head Neck Surg, 5, 4, 1994) the use of a Sharplan 15 Watt laser with scanner to create a recipient site of diameter 2 mm and depth up to 6 mm. A single patient was so treated, with minimal operative bleeding. A wide zone of coagulative necrosis of width 175 µm was created around the crater. Follow up data has not been published and graft viability is unknown.

The wide zone of hemostasis associated with use of the $CO_2$ laser is a consequence of the non-optimal choice of wavelength. At the $CO_2$ laser wavelength of 10.6 µm, tissue absorbs most of the energy within 50 µm although a wider tissue volume can be affected. This results in wider tissue injury and hemostasis than would be optimal. It is likely that the hemostasis associated with the use of the $CO_2$ lasers described above will also impair graft take viability, since such hemostasis is associated with a coagulative damage zone around the recipient site. The protracted erythematous period as noted is indicative of the cellular repair and angiogenic processes associated with significant wound formation. As a consequence of this wound formation, transplanted hair follicles may not receive sufficient nourishment during or subsequent to this healing phase.

This document describes a method and apparatus for skin ablation and for the reduction of the adverse effects associated with laser hair transplantation.

SUMMARY OF THE INVENTION

The present invention comprises a laser treatment method and apparatus for preparing recipient sites for implanting hair bearing tissue on the scalp.

The treatment method, according to one embodiment of the invention, includes:

irradiating a selected treatment site of alopecic scalp tissue with a pulsed coherent light having a wavelength substantially in the range of 2.5–3.5 µm, the light having an energy fluence substantially in the range of 1–200 J/cm², a pulsewidth substantially in the range of 100–2000 microseconds, and a spot area incident on the treatment site substantially in the range of $10^{-3}$ to $10^{-1}$ cm², controlling exposure duration at the treatment site of the light to produce with the irradiation a controlled ablation depth of 1–5 mm at the treatment site, directing the light to produce a plurality of recipient sites in said alopecic scalp tissue, whereby slit-shaped recipient sites are produced which are suitable for receiving transplanted grafts, wherein each of the slit-shaped sites is angled in a direction corresponding to a local prevalent direction of hair growth, and further directing the light to produce the recipient sites in an irregular grid pattern wherein the slit-shaped sites have adjacent positions which are linearly offset.

The effect of producing the slit-shaped recipient sites corresponding to the local prevalent direction of hair growth is illustrated in FIG. 1 which shows an alopecic scalp section (1), locally resident hairs within their germinative follicle (2), and a laser ablated recipient site (3).

The treatment method is further characterized by:

A regime of pre-medication to modify tissue healing response and minimize incidence of adverse effects.

Controlling hemostasis, as by using intra-dermal epinephrine containing (~1:200 000) anesthesia.

Allowing the skin to heal for a period of 2–16 weeks.

One apparatus for practicing the foregoing embodiment consists of a modified high power erbium laser system producing round or elliptical-shaped spots. This apparatus is further characterized by the availability of an angled stand-off to facilitate a non-orthogonal incidence of laser exposure. Such an angled exposure more closely approximates the direction of local hair growth, the apparatus is also provided with a port by which positive pressure flow of an inert gas can be introduced, thereby maintaining the integrity of local optics. An adjacent port may be used to introduce water flow to create a fine aerosol spray.

The invention incorporates a modified laser apparatus with new application, together with a novel treatment method for the ablation of tissue and for the preparation of viable sites for hair transplantation. The new treatment method thus developed presents the potential for numerous significant advantages, particularly relating to precision of ablation and to minimization of proximal site damage and precise removal (ablation) of alopecic scalp tissue. By comparison, the $CO_2$ laser has a much reduced absorption in tissue (by a factor of 10) and is less suited to precise ablation and fashioning of recipient sites. Creation of a well defined transplant site with minimal proximal damage in turn improves the prospect of viability of the grafted hair bearing tissue. This development of a clinically effective therapeutic treatment using a carefully controlled modified laser apparatus with associated minimization of adverse effects is a major improvement and advance over current options.

BRIEF DESCRIPTION OF THE DRAWINGS

For a fuller understanding of the nature and objects of the invention, reference may be had to the following detailed description and the accompanying drawing, in which.

DETAILED DESCRIPTION OF THE INVENTION

Figure 2:
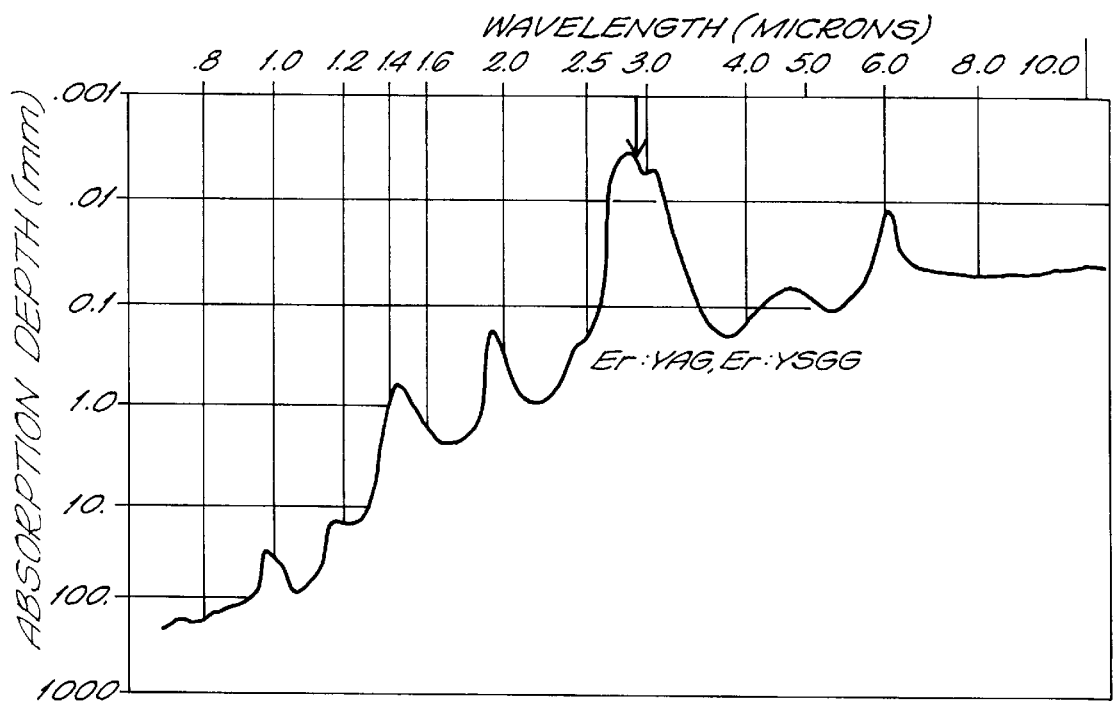
FIG. 2 is a graph illustrating absorption depth in water as a function of illuminating wave length.

Theoretical Considerations:

When selection of laser type is under consideration, the two most significant variables to consider are wavelength and pulsewidth. Wavelength defines depth of penetration of the light. As shown in FIG. 2, the wavelength of the erbium laser, around 2.9 $\mu$m, exhibits the highest degree of absorption in water, which is the principal constituent of skin tissue. Collagen, another significant constituent of skin tissue, also exhibits high absorption near 2.9 $\mu$m, with its local absorption peak at 3.03 $\mu$m. Use of a wavelength close to the 2.9 $\mu$m absorption peak of water leads to an efficient ablative process. By comparison, the $CO_2$ laser, with a tenfold diminished absorption coefficient, is a poor dermal ablation tool. The erbium laser has also been used to ablate hard dental tissue, which has a much lower water content in the range 2–13%.

Selection of pulsewidth is of equal importance. When hair transplant site preparation is underway, it is critical that the resultant heat production is unable to conduct widely into the surrounding dermis and thereby compromise follicular viability. This dictates that the applied pulse duration of the energy be well matched to the mechanical characteristics of the absorbing tissue volume. The concept of 'thermal relaxation time' has been introduced to describe the time period within which a target tissue area loses half of its heat. In the instance of a hair transplant site preparation, it is important that the energy be applied in a time period of less than 1 millisecond, well within the thermal relaxation time interval of the targeted tissue segment.

In accordance with the above criteria, a method has been developed in which a modified erbium laser, with optical beam delivery, focusing apparatus, and gas/fluid ports, is employed to prepare a host site for the transplantation of hair bearing tissue.

It is instructive to first review the superficial ablation of tissue using infrared lasers as described by previous researchers. Such work has centered on the study of the ablation of superficial lesions such as pigmented marks and benign tumors.

The application of superficial tissue ablation has been studied extensively by Professors Kaufmann and Hibst since 1989, who have published a number of papers (Kaufmann, R., Hartmann, A., Hibst, R., J. Dermat. Surg. Oncol. 1994, 20, 112–118.; Kaufmann, R., Hibst, R. 1990, Clin. Exp. Derm.; Hibst, R., Kaufmann, R. 1990, Las.Med.Sc., 6, 391–7.) Further work has been reported by Walsh (Walsh, A. J., and Cummings, C., 1994, Las. Surg. Med., 15(3), 295–305.).

In this section, results are compared and interpreted and open issues associated with the published literature are identified. This provides a useful background to the development of the new treatment method and apparatus to the application of more precise dermatological tissue removal and to the field of hair transplantation.

In early studies by Kaufmann, Hibst and Walsh, a relatively low power erbium laser was employed. This laser was capable of a pulse energy of 300 mJ, with maximum repetition rate of 5 Hz and fixed pulse width of 250 $\mu$sec. More recently, more powerful variants have been employed.

Kaufmann and Hibst have studied a number of different models, including animals, both in-vitro and in-vivo, and a limited number of in-vivo human patients presenting with epidermal and dermal lesions and tattoos.

In one of the above papers, the authors considered the application of multiple pulses at 1 Hz and 2 Hz on excised and in-vivo samples of pig skin. A 2 mm thickness of excised tissue was exposed with pulses of variable fluence at each of the two repetition rates. These measurements were used to plot induced crater depth per pulse as a function of fluence, for fluence levels up to 80 J/cm$^2$. These results indicated that an in-vitro skin thickness of up to 400 $\mu$m could be removed by a single pulse with a high fluence of up to 80J/cm$^2$. The results further indicated that higher repetition rates might compromise the ablation achieved per pulse, since maximum per pulse ablation was found to be reduced to approximately 320 $\mu$m at 2 Hz. The in-vivo portion of this study demonstrated minimal coagulation around the resultant crater, of magnitude less than 200 $\mu$m in all cases. Further, width of damage zone did not correlate with applied energy density (it should be noted here that later work by Walsh did find a slight correlation between fluence and damage zone width). The authors concluded that the use of high radiant exposures increases ablation rate without an accompanying deleterious increase in proximal damage.

Absent from some of this work is a detailed correlation between in-vitro and in-vivo ablation rates. The impact of any bleeding during ablation is thus neglected and the likely precise compromise in ablation rate unidentified. Also absent from this early work is an extension of the ablation measurements to the 5 Hz repetition rate available with the laser used. It was therefore not clear if the trend in reduced ablation per pulse would continue as repetition rate increased to 5 Hz or beyond. The issue would be further complicated in the in-vivo situation by the rate at which blood flows into the crater. These issues are inadequately addressed in the published literature.

In all exposures reported in the earlier papers, the authors noted an absence of hemostasis associated with the use of the Erbium laser, resulting from the narrow width of proximal coagulation (typically around 50 $\mu$m in width). Further, concurrent saline cleaning was required to remove blood ingress. The impact of this process on total ablation time was not presented. Rapid healing of the Erbium induced wounds was noted, similar to that found with scalpel incisions. Re-epithelialization occurred in less than 7 days. The effects of current generation higher repetition rates available on current systems might further introduce a measure of hemostasis not seen in early experiments. Indeed, unpublished reports of hemostatic potential are emerging from several sources.

In a 1994 paper (Kaufmann, R., Hartmann, A., Hibst, R., J. Dennat. Surg. Oncol., 20, 112–118), the authors compare a number of IR lasers (Ho, Tm, Er, CO$_2$) as ablative tools on pig skin in vivo. Compared to the other lasers studied, the Erbium laser was found to result in minimal wound healing processes of granulation tissue formation and inflammatory infiltration, and to re-epithelialize more rapidly. Incidence of these processes can be related to degree of trauma during the initial wound creation process. Maximum repetition rate of the Erbium laser as used in this study was 10 Hz. The authors noted that use of a fluence around threshold, together with high repetition rate, resulted in tissue desiccation and significant coagulation. This resulted from the complete transformation of all the laser energy to heat, in a cumulative fashion. At low repetition rates generally, a tedious ablation process resulted, although the authors noted that increased repetition and higher fluence led to a more efficient process. At higher fluence (250 mJ in a 1 mm spot, equating to approximately 32 J/cm$^2$), an ablation crater depth of approximately 40 $\mu$m was produced. The authors further speculated that the Erbium laser had the promise of versatility in degree of hemostasis, as repetition rate and fluence were increased.

When the reported work is reviewed as a whole, and thresholds and ablation rates derived, several discrepancies emerge and it becomes apparent that a number of questions remain unanswered. Contradictions are apparent in the published literature and the optimum method of extension of the parameters previously applied is not addressed in the context of the deep tissue ablation requirement of the hair transplantation application. Further, the previously published dermatological work basically addresses only the removal of superficial lesions, rather than the precise sculpting of crater shapes and orientations as would be required for the application of hair transplant site preparation.

A wide variance in ablation rate was reported by these authors, from as little as 1 $\mu$m/J/cm$^2$ to as much as 5 $\mu$m/J/cm$^2$. The higher figure was an in-vitro ablation rate at low repetition, uncomplicated by the ingress of blood. In-vivo rates varied from 1–3 $\mu$m/J/cm$^2$ under single pulse conditions. Such single pulse conditions should obviate the impact of blood ingress on the 250 $\mu$s time scale and greater comparability with the bloodless in-vitro situation would be expected. No explanation is presented for the deviation between in-vivo and in-vitro results, although the higher tensile stress under which the in-vivo samples were situated would also explain part of the higher threshold and hence lower ablation rate. Limited evidence has also been presented that ablation rate per pulse has a repetition rate dependence, although this dependence is not addressed in detail.

The in-vitro ablation rates correlate reasonably well with those reported by Walsh (Walsh, A. J., and Cummings, C., 1994, Las. Surg. Med., 15(3), 295–305.). At high fluence in the range 20–60 J/cm$^2$, an ablation rate of 1–3 $\mu$m/J/cm$^2$ was reported. At fluence levels in the 60–80 J/cm$^2$ region, Walsh noted the induction of a limiting plasma, which defined maximum fluence. Walsh did note, however, an increase in width of thermal damage zone at higher fluence.

The present invention determines the appropriate minimum ablation rate per pulse which would result from the use of the higher energy more repetitious Erbium lasers now available.

Figure 1:
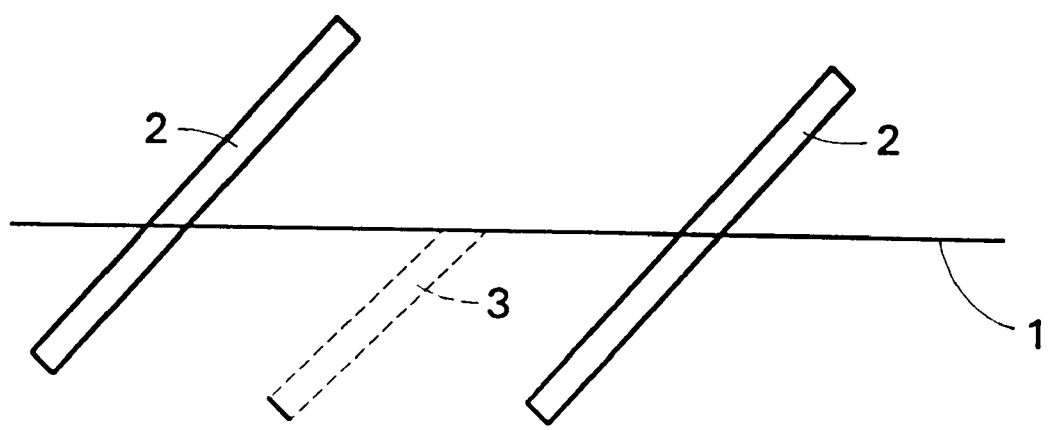
FIG. 1 is a representation of a recipient site including slits for receiving graft transplants formed from a non-orthogonal incident of laser exposure in the practice of the invention where each of the slits are angled in a direction corresponding to a local prevalent direction of hair growth.

If a (minimum) ablation rate of 1 $\mu$m/J/cm$^2$ is assumed and a 1000 mJ system operating at 15 Hz with 1 mm spot size is used (fluence of 127 J/cm$^2$ per pulse), a theoretical minimum ablation rate of 120 $\mu$m per pulse can be predicted. A minimum cumulative ablation rate of up to 1.8 mm/sec would then be expected from this extrapolation of clinical data. This would provide an adequate incision depth for site preparation within about 2 seconds. In practice, this parameter set could be used to quickly ablate a single circular recipient site, or several adjacent recipient sites resulting in a longitudinal slit. The sites would then 'gape' somewhat under the influence of local lines of tissue tension. It is hence important that initial exposure site dimensions be less than ultimately required especially in the direction parallel to that of local lines of tissue tension. It is also important that the laser beam be angled, as shown in FIG. 1, consistent with the local directional lines of hair growth to provide recipient sites, each of which are slit-shaped and formed in the alopecic tissue.

Higher repetition rates produce a greater hemostatic effect, although the required degree of hemostasis for hair transplantation is minimal. Simple clinical experiments performed by the author (unpublished) indicate that presence of blood does not significantly affect clinical outcome under the regime described above, although operator pathogen exposure risk increases. Concurrent use of smoke evacuation, as practiced with superpulsed $CO_2$ lasers, minimizes interference and safety risk from particulate debris.

From the foregoing it has become apparent that a laser source emitting in the wavelength region 2.5–3.5 $\mu$m, with variable pulsewidth and spot size capabilities, has potential for dermatological tissue ablation. This invention addresses the harnessing of these basic principles by means of appropriate apparatus and treatment method development to produce optimal therapeutic results. In particular, it is believed that the subject matter of this invention will improve the precision of ablation and will meet the conditions required for the ablative preparation of a recipient site for transplantation of hair bearing tissue grafts. It is important that the source be a laser, with its attendant coherence, rather than an incoherent source such as, for instance, a flashlamp-based source. Coherent light is unidirectional in nature and better suited to precise targeting of human tissue.

Further, adverse sequelac associated with currently available technologies will be reduced under the practice of this invention. In particular, a reduction in the extent of the proximal tissue coagulation and necrosis associated with use of the $CO_2$ laser is likely, leading to enhanced graft viability. In addition, the physical ablation and removal of alopecic scalp will allow for an ultimately higher density of hair on the formerly alopecic section of scalp. A careful angling of the exposing laser beam will further allow graft tissue to be implanted in a direction consistent with that of local hair growth.

It is useful to consider prior reported use of the erbium laser to ablate other body constituents, such as hard dental tissue. Hard dental tissue such as enamel and denting present lower water content (2% and 13% respectively) than skin tissue (approximately 70%), and accordingly exhibit less favorable ablation when exposed to wavelengths which are highly absorbed in water, such as those in the range 2.5–3.5 $\mu$m. As a consequence, use of the erbium laser on dry hard dental tissue is associated with poor ablation efficiency and wide lateral thermal damage. Adjunctive use of a fine layer of water is described by Burkes (Burkes, E. J., et. aL, Jour. Pros. Dent., 1992, 67, 847–851), Hibst (Hibst. R., Keller, U.; SPIE vol. 2623, p.139–144) and Lukac (Lukac, M., SPIE vol. 2080, pp. 51–54). Burkes notes that presence of a water film of the appropriate thickness directly enhances ablation of enamel and denting adjunctive to the expansion of the water vapor as it absorbs energy. Hibst and Lukac comment that the water film may spare underlying tissue by drawing heat away from the site, although Lukac notes a slight reduction in ablation rate, contrary to the findings of Burkes.

The author of this application is unaware of any reported use of adjunctive water spray to assist the ablation process in dermatological applications. Instead, water has been used to irrigate and clean debris from the treatment site. In this invention, the apparatus is modified to include a fine water spray, which the author believes will improve ablation efficiency and which will reduce lateral tissue damage, even in high water content dermatological tissue.

The above represents a summary of the theoretical considerations employed to calculate an appropriate parameter set, apparatus design and treatment method. As part of this invention, an Erbium laser is used to effect the optimal treatment method devised here. The laser handpiece is further characterized by an angled beam delivery, facilitated by an angled stand-off, and by an available elliptical spot shape, for improved cosmesis. The handpiece also has gas and liquid entry ports.

General Treatment Procedures and Preferred Details:

The treatment site and patient are first medicated. Epinephrine (1:200,000) should be used to reduce bleeding during site preparation. Other medications may be applied over a longer period of time to modify the healing response of the tissue and reduce incidence of adverse effects.

An energy fluence in the range 1–200 $J/cm^2$ and pulsewidth in the range 100–2000 microseconds, will typically be used. The recipient site may be prepared with a single circular or elliptical exposure spot with area in the range $10^{-3}$ to $10^{-1}$ $cm^2$, or with several spots constituting an elongated slit. Multiple pulses are applied to each site, until the physician determines that an adequate crater depth has been realized. Coherent pulsed light with wavelength in the range 2.5–3.5 $\mu$m is used, with a wavelength of 2.94 $\mu$m being optimal. A concurrent water spray may be applied.

Figure 5:
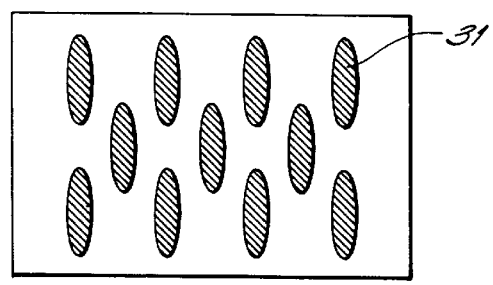
FIG. 5 shows adjacent recipient sites linearly offset over the area of an alopecic scalp, according to the practice of the invention.

Many such sites are prepared over the area of alopecic scalp. Adjacent sites (31) are linearly offset, as shown in FIG. 5.

Transplanted hair bearing tissue segments are then placed in the craters. One preferred specification for the treatment device is listed below:

Host material: Er:YAG

Wavelength range: 2.94 $\mu$m pulsewidth: 0.1–2.0 milliseconds exposure fluence: 1–200 $J/cm^2$ repetition rate: 1–20 Hz.

spot area on skin: 0.001–0.1 $cm^2$, variable spot shape on skin: round, elliptical or rectangular delivery system: fiber, with dermatology handpiece termination handpiece: designed for angled or normal application of light handpiece features: optional administration of inert gas and water aiming beam: red diode or helium neon laser (1–10 mW)

This preferred embodiment can specifically be utilized for the preparation of angled recipient sites for hair bearing excised scalp tissue.

A second alternative embodiment employs the use of a different host material containing Erbium ions, such as Er:YSGG.

Figure 3:
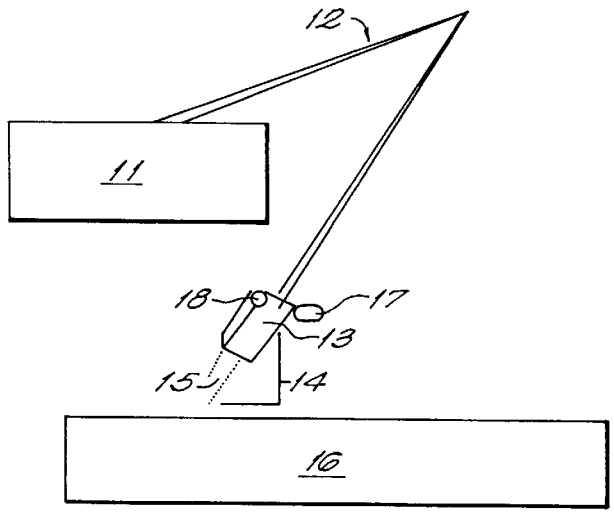
FIG. 3 shows a therapeutic treatment device having laser head cabinetry containing a laser source, an articulated arm or fiber delivery system, a handpiece containing focusing lenses, an angled standoff distance gauge, a gas port for introducing positive pressure flow of inert gas and an adjacent irrigation port for introducing water flow, according to an embodiment of the invention.

This first preferred embodiment is sketched as FIG. 3:

In practice, a separate footswitch (not shown) provides triggering to the laser source found within the laser head cabinetry (11). The source incorporates a flashlamp-pumped rod containing active Erbium ions. Light from this rod is directed along an articulated arm or fiber delivery system (12) to a handpiece containing focusing lenses (13). These lenses, together with an available angled standoff distance gauge (14), provide precise positioning and focusing of the treatment beam (15) onto the patient's skin (16). An inert 'purging' gas is directed through the handpiece from an inlet (17) to keep the treatment area and local focusing lenses clear of debris. A fine water spray is introduced via port (18), adjacent to the purging gas inlet. An incorporated visible 'aiming beam', within the cabinetry enclosure, also delivered through the light guide, provides verification of the ultimate placement of the invisible treatment laser spot.

Figure 4:
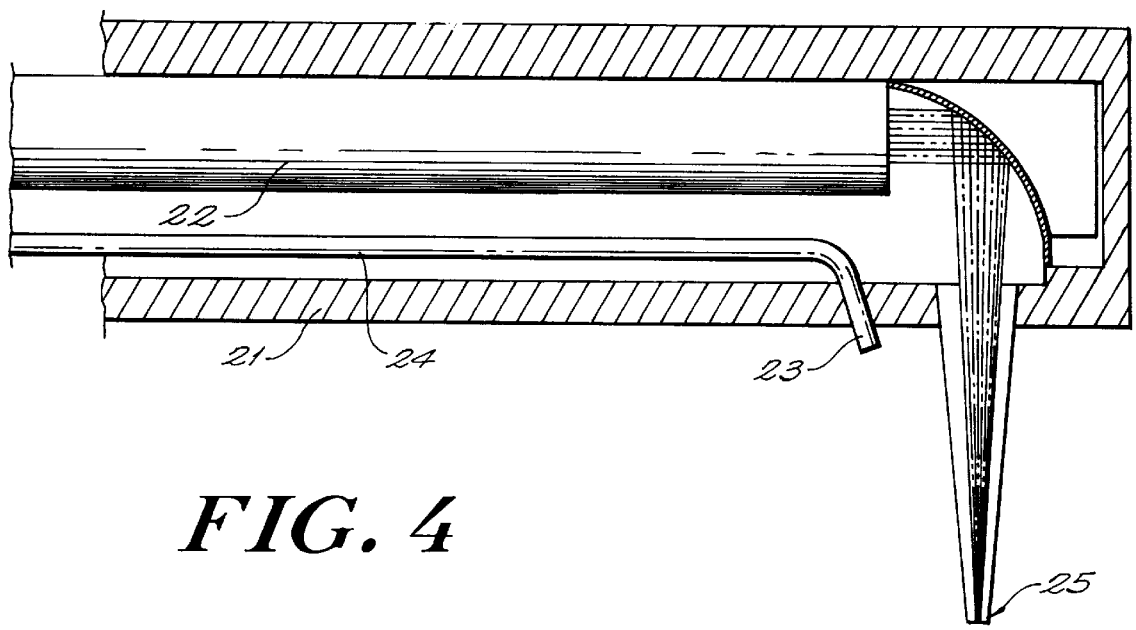
FIG. 4 shows a distal beam delivery device having an articulated delivery system and a small diameter water flow tube terminating in a fine nozzle. according to an embodiment of the invention.

Further detail of one embodiment of the distal beam delivery apparatus is shown in FIG. 4. Here, the distal end of the articulated arm is shown (21), together with the internally propagating beam (22). A small diameter water flow tube (24) is shown, terminating in a fine nozzle (23). The beam is focused onto the tissue at a focal point (25).

Clinical Treatment Methodology

The goal of the treatment is to precisely prepare angled recipient sites with minimal adjacent thermal coagulative damage. Below is presented an optimal and novel therapeutic treatment methodology suitable for such a clinical application.

Dermatological Applications:
(i) Preparation of precise recipient sites for hair transplantation.
(ii) Precise dermatological tissue ablation.

A number of major advantages and conveniences are provided by the present treatment method, including:

1. The present methodology envisages the use of a specific parameter set chosen to provide optimum selectivity of damage to and ablation of the target tissue only. This precision results from the optimal absorption of the Erbium wavelength and the limited conduction which results from the short microsecond domain pulsewidth. An optional water spray may also be introduced to enhance ablation precision and minimize lateral damage. Minimal adjacent damage provides maximum opportunity for viability of the transplanted graft.
2. Alopecic scalp is actually removed, rather than pushed aside, resulting in an opportunity for maximum ultimate transplanted hair density in terms of ratio of hair bearing to alopecic scalp.
3. Angled application of narrow band coherent light provides for recipient site orientation parallel to that of local hair growth, for optimum cosmesis.
4. The procedure is relatively rapid and efficient and may be suitable for future automation, in which an irregular grid structure could be created by scanning the beam over an alopecic area.

General Treatment Procedures and Preferred Details:

The treatment method, according to one embodiment of the invention, includes:

irradiating a selected treatment site of alopecic scalp tissue with a pulsed coherent light having a wavelength substantially in the range of 2.5–3.5 μm, the light having an energy fluence substantially in the range of 1–200 J/Cm$^2$, a pulsewidth substantially in the range of 100–2000 microseconds, and a spot area incident on the treatment site substantially in the range of $10^{-3}$ to $10^{-1}$ cm$^2$, controlling exposure duration at the treatment site of the light to produce with the irradiation a controlled ablation depth of 1–5 mm at the treatment site, directing the light to produce a plurality of recipient sites in said alopecic scalp tissue, whereby slit-shaped recipient sites are produced which are suitable for receiving transplanted grafts, wherein each of the slit-shaped sites is angled in a direction corresponding to a local prevalent direction of hair growth (FIG. 1), and further directing the light to produce the recipient sites in an irregular grid pattern wherein the slits having adjacent positions are linearly offset.

The treatment method is further characterized by:

Controlling hemostasis using intra-dermal epinephrine containing (1:200 000) anesthesia.

Allowing the skin to heal for a period of 2–16 weeks.

Detailed Protocol

For a period of up to several weeks prior to treatment, the patient may be premedicated with retinoic acid to speed healing, hydroquinone to reduce local pigmentary response, and/or a viral agent such as acyclovir.

The recipient scalp area to be treated is photographed under controlled conditions. It is further examined to detect the presence of scarring or otherwise abnormal color or texture.

Individual sites are designated and marked on the scalp. Each site is then exposed with a chosen parameter set under optional irrigation. A typical parameter set would be: 1000 mJ energy, 1 mm circular spot size (approximately 127 J/cm$^2$), 15 Hz repetition rate, wavelength 2.94 μm, pulsewidth 300 μsec. Another typical parameter set would be: 600 mJ of energy, 0.75 mm spot size (approximately 140 J/cm$^2$), 10 Hz repetition rate, wavelength 2.94 μm, pulsewidth 300 μsec. Exposure would be effected for 1–2 seconds, resulting in a crater of depth approximately equal to 1–5 mm. Several such adjacent spots would be placed resulting in a single slit-shaped recipient site of approximate size 1×3 mm.

The resultant site will be inspected to ensure that a clean crater edge has been produced, with little evident charring. Charring is indicative of local thermal damage and may be reduced as appropriate in adjacent sites by reducing the applied fluence or by reducing the repetition rate.

Following treatment, a topical antibiotic and/or antiviral ointment may be applied to the treated site and the skin area covered with a dressing.

The patient will return several times after treatment for evaluation and assessment of graft viability. These visits will typically occur at intervals of 3 days, 1 week and thereafter monthly.

We claim:

1. A laser treatment method for the preparation of plural recipient sites for implanting hair-bearing tissue on skin of a human, said method comprising the successive steps of premedicating a selected treatment site of a patient with a medicament;

irradiating said selected treatment site of alopecic scalp tissue with erbium pulsed coherent light having a wavelength substantially in the range of 2.5–3.5 μm, said light having an energy fluence substantially in a range of 1–200 J/cm$^2$, a pulsewidth substantially in a range of 100–2000 microseconds, at a non-orthogonal angle incident to said treatment site and a spot area incident on said treatment site substantially in a range of $10^{-3}$ to $10^{-1}$ cm$^2$;

controlling exposure duration at said treatment site to produce a controlled ablation depth of 1–5 mm at said treatment site;

directing said light with a distance gauge for non-orthogonal administration of energy to produce a plurality of recipient sites in said alopecic scalp tissue, whereby slit-shaped recipient sites are produced which are suitable for receiving transplanted grafts, wherein each of said slit-shaped sites is angled in a direction corresponding to a local prevalent direction of hair growth; and further directing said light to produce said recipient sites in an irregular grid pattern wherein said slits have adjacent positions which are linearly offset.

2. The method according to claim 1, further comprising the step of irrigating said treatment site with a cooling fluid concurrently with said irradiating step.

3. The method according to claim 2, further comprising the step of introducing a flow of inert gas directed at a handpiece connected to a source of said light to reduce collection of debris on said source.

4. The method according to claim 1, wherein said medicament speeds healing about said treated site.

5. The method according to claim 4, wherein said medicament is retonoic acid.

6. The method according to claim 1, wherein said medicament reduces local pigmentary response about said treated site.

7. The method according to claim 6, wherein said medicament is hydroquinone.

8. The method according to claim 1, wherein said medicament is an antiviral agent.

9. The method according to claim 8, wherein said medicament is acyclovir.

10. The method according to claim 1, wherein said medicament reduces bleeding about said treated site.

11. A laser treatment method for ablation of human skin, said method comprising the successive steps of premedicating a selected treatment site of a patient with a medicament;

irradiating said selected treatment site of alopecic scalp tissue with erbium pulsed coherent light having a wavelength substantially in the range of 2.5–3.5 μm, said light having an energy fluence substantially in a range of 1–200 J/cm$^2$, a pulsewidth substantially in a range of 100–2000 microseconds, with a distance gauge for administration of energy at a non-orthogonal angle incident to said treatment site and a spot area incident on said treatment site substantially in a range of $10^{-3}$ to $10^{-1}$ cm$^2$; and irrigating said treatment site with a cooling fluid concurrently with said irradiating step.

12. The method according to claim 11, further comprising the step of introducing a flow of inert gas directed at a handpiece connected to a source of said light to reduce collection of debris on said source.

13. The method according to claim 11, wherein said medicament speeds healing about said treated site.

14. The method according to claim 13, wherein said medicament is retonoic acid.

15. The method according to claim 11, wherein said medicament reduces local pigmentary response about said treated site.

16. The method according to claim 15, wherein said medicament is hydroquinone.

17. The method according to claim 11, wherein said medicament is an antiviral agent.

18. The method according to claim 17, wherein said medicament is acyclovir.

19. The method according to claim 11, wherein said medicament reduces bleeding about said treated site.

20. The method according to claim 11, further comprising the step of irrigating said treatment site with a water spray to enhance ablation precision, concurrently with said irradiating step.

21. The method according to claim 11, wherein said cooling fluid is a spray.

22. The method according to claim 21, wherein said cooling fluid is water.

23. A therapeutic treatment device for ablation of skin tissue comprising a laser head having a controllable laser and a cooling unit for providing a cooling fluid at a dermal treatment site of irradiation by said laser an articulated delivery system connected to said laser head terminated in a handpiece containing a focusing optics element and a distance gauge.

* * * * *

UNITED STATES PATENT AND TRADEMARK OFFICE
CERTIFICATE OF CORRECTION

PATENT NO.  : 6,022,345
DATED       : February 8, 2000
INVENTOR(S) : Iain D. Miller and Karolj Nemes It is certified that error appears in the above-identified patent and that said Letters Patent is hereby corrected as shown below:

Column 1,
Line 54, please replace "W.P., Jourm." with -- W.P., Journ --;

Column 2,
Line 1, please replace "W.P., Jourm." with -- W.P., Journ --.;

Column 4,
Line 1, please replace "a fine nozzle. according to" with -- a fine nozzle, according to --;

Column 5,
Line 53, please replace "R., J. Dennat" with -- R., J. Dermat --;

Column 7,
Line 23, please replace "sequelac" with -- sequelae --;
Line 36, please replace "denting" with -- dentin --;
Line 44, please replace "E.J., et. aL," with -- E.J., et. al., --;
Line 49, please replace "denting" with -- dentin --;

Column 9,
Line 45, please replace "1-200J/Cm$^2$," with -- 1-200J/cm$^2$ --;

Signed and Sealed this

Twenty-fifth Day of June, 2002

*Attest:*

JAMES E. ROGAN
*Attesting Officer*       *Director of the United States Patent and Trademark Office*